(12) United States Patent
Walker et al.

(10) Patent No.: US 10,058,646 B2
(45) Date of Patent: Aug. 28, 2018

(54) BLOOD BAG SYSTEM AND PROCESS FOR THE INACTIVATION OF PATHOGENS IN PLATELET CONCENTRATES BY USE OF THE BLOOD BAG SYSTEM

(71) Applicant: MACO PHARMA S.A., Mouvaux (FR)

(72) Inventors: Wolfram Hubert Walker, Rödermark (DE); Frank Tolksdorf, Ober-Ramstadt (DE); Thierry Verpoort, Halluin (FR); Francis Goudaliez, Faches Thumesnil (FR)

(73) Assignee: MACO PHARMA S.A., Mouvaux (FR)

( * ) Notice: Subject to any disclaimer, the term of this patent is extended or adjusted under 35 U.S.C. 154(b) by 18 days.

(21) Appl. No.: 15/450,375

(22) Filed: Mar. 6, 2017

(65) Prior Publication Data

US 2017/0232163 A1 Aug. 17, 2017

Related U.S. Application Data

(62) Division of application No. 12/311,033, filed as application No. PCT/EP2007/005538 on Jun. 22, 2007.

(30) Foreign Application Priority Data

Sep. 19, 2006 (EP) .................................. 06019589

(51) Int. Cl.
*A61K 41/00* (2006.01)
*A61J 1/10* (2006.01)
(Continued)

(52) U.S. Cl.
CPC ......... *A61M 1/0272* (2013.01); *A61L 2/0047* (2013.01); *A61M 1/0209* (2013.01);
(Continued)

(58) Field of Classification Search
CPC ............. A61L 2202/22; A61L 2202/23; A61L 2/0047; A61M 1/0209; A61M 1/0272;
(Continued)

(56) References Cited

U.S. PATENT DOCUMENTS

| 4,469,227 A | 9/1984 | Faust |
| 4,586,928 A | 5/1986 | Barnes et al. |

(Continued)

FOREIGN PATENT DOCUMENTS

| CA | 2634296 | 12/2006 |
| DE | 298 01 590 U1 | 5/1998 |

(Continued)

OTHER PUBLICATIONS

Prodouz et al., "Use of Laser-UV for Inactivation of Virus in Blood Products," Blood, vol. 70, No. 2, (Aug. 1987), pp. 589-592; National Institutes of Health, Bethesda, MD.

(Continued)

*Primary Examiner* — Dirk Bass
(74) *Attorney, Agent, or Firm* — Locke Lord LLP; Alan B. Clement; Peter J. Fallon

(57) ABSTRACT

The present invention relates to a blood bag system, a method for its manufacture, and a process for reducing pathogens and leucocytes in biological fluids in particular in therapeutic quantities of platelet concentrates (PC) contained in the blood bag system, using UV-light and agitation, wherein part of the plasma of the PC is optionally exchanged against a platelet additive solution.

33 Claims, 3 Drawing Sheets

(51) Int. Cl.
| | |
|---|---|
| *B65B 3/04* | (2006.01) |
| *B65B 55/16* | (2006.01) |
| *A61M 1/02* | (2006.01) |
| *A61M 1/36* | (2006.01) |
| *B65B 7/02* | (2006.01) |
| *B65B 55/08* | (2006.01) |
| *A61L 2/00* | (2006.01) |

(52) U.S. Cl.
CPC ............ *A61M 1/3681* (2013.01); *B65B 7/02* (2013.01); *B65B 55/08* (2013.01); *B65B 55/16* (2013.01); *A61L 2202/22* (2013.01); *A61L 2202/23* (2013.01); *A61M 2207/00* (2013.01)

(58) Field of Classification Search
CPC . A61M 1/3681; A61M 2207/00; B65B 55/08; B65B 55/16; B65B 7/02
USPC .......... 53/409; 210/748.11; 604/408
See application file for complete search history.

(56) References Cited

U.S. PATENT DOCUMENTS

| | | | |
|---|---|---|---|
| 4,630,448 | A | 12/1986 | Bilstad et al. |
| 4,952,812 | A | 8/1990 | Miripol et al. |
| 4,952,818 | A | 8/1990 | Erdelyi et al. |
| 5,030,200 | A | 7/1991 | Judy et al. |
| 5,625,079 | A | 4/1997 | Wollowitz et al. |
| 6,139,878 | A | 10/2000 | Summaria et al. |
| 6,268,120 | B1 | 7/2001 | Platz et al. |
| 6,686,480 | B2 | 2/2004 | Wollowitz et al. |
| 7,025,877 | B1 | 4/2006 | de Gheldere et al. |
| 2001/0046450 | A1 | 11/2001 | Laub et al. |
| 2002/0043051 | A1 | 4/2002 | Manica et al. |
| 2002/0138066 | A1 | 9/2002 | Manica et al. |
| 2003/0064001 | A1 | 4/2003 | Fries et al. |
| 2003/0072676 | A1 | 4/2003 | Fletcher-Haynes et al. |
| 2003/0228564 | A1 | 12/2003 | Edrich et al. |
| 2004/0186410 | A1 | 9/2004 | Davidner et al. |
| 2005/0202395 | A1 | 9/2005 | Edrich et al. |
| 2007/0164233 | A1 | 7/2007 | Mohr |
| 2009/0155121 | A1 | 6/2009 | Mohr et al. |
| 2009/0187117 | A1 | 7/2009 | Imai |
| 2010/0178200 | A1 | 7/2010 | Walker et al. |

FOREIGN PATENT DOCUMENTS

| | | |
|---|---|---|
| DE | 10 2005 062 410 A1 | 8/2007 |
| EP | 0 542 221 A1 | 5/1993 |
| EP | 0 933 090 A1 | 8/1999 |
| EP | 1 002 512 A2 | 5/2000 |
| EP | 1308172 | 5/2003 |
| EP | 0727938 | 6/2003 |
| EP | 0 933 090 B1 | 7/2006 |
| FR | 2 887 335 A1 | 12/2006 |
| JP | 09-108333 | 4/1997 |
| JP | 2005-052239 | 3/2005 |
| WO | WO 1989/09067 | 5/1989 |
| WO | WO 95/12973 | 5/1995 |
| WO | WO 2001/54738 | 2/2001 |
| WO | WO 2001/54739 | 2/2001 |
| WO | WO 01/96340 | 12/2001 |
| WO | WO 02/26270 | 4/2002 |
| WO | WO 02/32469 A2 | 4/2002 |
| WO | WO 2002/092806 | 11/2002 |
| WO | WO 03/036915 A1 | 8/2003 |
| WO | WO 03/086479 A1 | 10/2003 |
| WO | WO 2003/090795 | 11/2003 |
| WO | WO 2004/032782 A1 | 4/2004 |
| WO | WO 2004/083081 | 4/2004 |
| WO | WO 2005/089816 | 9/2005 |
| WO | WO 2006/136698 A2 | 12/2006 |
| WO | WO 07/076832 | 7/2007 |
| WO | WO 08/034476 | 3/2008 |

OTHER PUBLICATIONS

Andreu et al., "Ultraviolet Irradiation of Platelet Concentrates: Feasibility in Transfusion Practice," Transfusion, vol. 30, No. 5 (1990), pp. 401-406.

Pamphilon, Derwood H., "The Rationale and Use of Platelet Concentrates Irradiated With Ultraviolet-B Light," Transfusion Medicine Reviews, vol. 13, No. 4 (Oct. 1999), pp. 323-333.

Platelets Study Group, "Leukocyte Reduction and Ultraviolet B Irradiation of Platelets to Prevent Alloimmunization and Refractoriness to Platelet Transfusions," The New England Journal of Medicine, (Dec. 25, 1997), vol. 337, No. 26, pp. 1861-1869.

Kallenbach, "Inactivation of Viruses by Ultraviolet Light," Morgenthaler J-J(ed), Virus Inactivation in Plasma Products, Curr. Stud. Hematol Blood Transfus. Basel. Karger 1989, No. 56, pp. 70-82.

Hart et al., "Inactivation of Viruses during Ultraviolet Light Treatment of Human Intravenous Immunoglobulin and Albumin," Vox Sang, (1993), 64:82-88.

Chin, "Virucidal Short Wavelength Ultraviolet Light Treatment of Plasma and Factor VIII Concentrate: Protection of Proteins by Antioxidants," Blood, vol. 86, No. 11 (Dec. 1, 1995), pp. 4331-4336.

Handbook of Transfusion Medicine, 4th Edition, Published 2007, Edited by DBL McClelland, Scottish National Blood Transfusion Service, Edinburgh, Published by United Kingdom Blood Services, ISBN 0113226772.

Advisory Action and Decision for Dismissal of Amendment and their English translations.

BLOOD BAG SYSTEM AND PROCESS FOR THE INACTIVATION OF PATHOGENS IN PLATELET CONCENTRATES BY USE OF THE BLOOD BAG SYSTEM

The present invention relates to a blood bag system, a method for its manufacture and a process for reducing pathogens and leucocytes in biological fluids in particular in therapeutic quantities of platelet concentrates (PC).

The presence of potentially pathogenic materials such as viruses and/or bacteria in biological fluids is of great concern for many protocols, particularly those involving the processing of blood and/or blood components, e.g. to obtain transfusion products to be administered to patients. A number of diagnostic tests are developed and routinely used to assure viral and bacterial safety of blood products. Despite intense testing, it is difficult to assure the required degree of absence of pathogens in blood products. Pathogens exist in human blood donations and may lead to infectivity at the recipient. It is therefore required to find and use save procedures which allow the destruction and/or removal of such pathogens in human blood or blood products.

The present invention relates to the viral and bacterial safety of platelet concentrates. Platelet concentrates are commonly prepared from human blood donation by apheresis techniques or by a so called "buffy-coat pooling technique". Both methods result in platelet concentrates, which commonly contain between 2 to $5 \times 10^{11}$ platelets in a plasma volume of 100 to 400 ml. Such blood products are called platelet concentrates and are suitable for therapeutic applications in patients with platelet deficiencies.

Platelet concentrates are generally stored in blood banks in liquid state commonly at room temperature and for a defined period of time. It is desirable to perform pathogen reduction before storage to avoid increase of pathogen concentration during storage. Furthermore, blood banks are interested in increasing the shelf life time of platelet concentrates to allow for the necessary availability of such blood products considering the average amount donated versus the total used in transfusion in peak times.

PRIOR ART SECTION

In the literature a number of blood bag arrangements have been suggested for storing and treating blood products.

EP 0 933 090-A discloses a blood bag system for storing blood components comprising photosensitizers. The blood bag system comprises a leucocyte filter and tubing connecting the filter with two blood bags. One blood bag comprises the blood product in need for viral inactivation, the other is intended to comprise the mixture of the blood product and the photoactive compound. The system furthermore allows for removal of the photoactive compound and if necessary its photoproducts generated during irradiation.

French patent application FR 200506296 describes a blood bag system for the storage of platelet concentrates, which allows sampling of the platelet concentrates through an integrated sampling bag whereby detections of pathogens in the blood or the platelet concentrates are possible.

US 2001/0046450 A1 discloses a method and an apparatus for inactivating contaminants in blood products. The blood product is guided past a source of UV-C radiation whereby the flow of the blood product is controlled to receive irradiation doses of lower than 640 J/m². The blood product is substantially free of non-enveloped viruses after the irradiation. The apparatus includes an emitter of type C ultraviolet radiation placed so as to emit type C radiation toward the blood product in a quartz tube of a tube made of polymer material which does not absorb type C radiation. The apparatus also includes a flow meter for controlling the flow rate of the blood product to be treated.

German patent application 10 2005 062 410.3, filed 23 Dec. 2005 by the present applicant as co-applicant, teaches a process for the reduction of pathogens and/or leucocytes in platelet concentrates using flexible UV-transparent blood bags, the contents of which is made of full reference for the present application. The flexible blood bags are irradiated while agitating the bag.

US 2003/0228564 discloses a method of inactivating pathogens in blood and blood components by adding riboflavin and nitric oxide in the blood or blood components and irradiating under agitation the blood or blood component with UV or visible light. The Sengewald bag used in the method is not designed to avoid dead areas during the irradiation.

OBJECT OF THE INVENTION

It is an object of the present invention to provide a blood bag system to carry out a procedure for effectively inactivating pathogens in platelet concentrates without adversely affecting the platelet concentrate. Pathogens like viruses, bacteria, spores, fungi, protozoa as well as leucocytes shall be inactivated to an extend to allow save storage of the platelet concentrates at room temperature and in liquid state for several days without impairing the therapeutic efficiency of the concentrates.

Another object of the present invention is to develop a disposable plastic bag system, comprising one or more bags for illuminating the PC and for the storage and transfusion of the platelet concentrate.

SUMMARY OF THE INVENTION

Surprisingly it was found that by use of the blood bag system according to the subject matter of the claim 1 and the independent process/method claim, and as further defined in the sub claims or hereinafter, effective inactivation of viruses, bacteria, protozoa, spores and reduction of leucocytes can be achieved without the addition of any pathogen inactivating substance.

It is further part of the present invention to optionally substitute part of the plasma contained in the PC by a platelet storage solution to form a suspended PC. In the suspended PC contained in the blood bag, at least 20 weight %, most preferred 70% of the plasma content of the platelet concentrates is exchanged against a platelet storage solution.

It is further part of the present invention that the platelet concentrate treated as described above can be stored for an extended time without impairment of the platelet quality.

DESCRIPTION OF THE PREFERRED EMBODIMENTS

The blood bag system comprises either one bag for irradiation with UV light and storage of a suspended PC, wherein the irradiation bag forms at the same time the storage bag, or comprises a first bag for irradiation (irradiation bag) with UV light and a second bag (storage bag) for storage wherein in each of the different blood bag systems the irradiated suspended PC can be stored for up to 10 days without clinically significant reduction of the therapeutic quality.

According to a preferred embodiment the blood bag system according to the invention comprises a leucodepletion filter for leucodepletion of the inlet stream of non-irradiated PC. The leucodepletion filter for above purpose is preferably incorporated in the inlet tubing of the irradiation bag.

The irradiation bag is made from an UV-transparent plastic material. Suitable polymer materials are polyolefins and ethylene vinyl acetate (EVA), extruded or calendered to wall thicknesses of 0.8 mm or less, in particular about 0.5 mm or less. The plastic foils obtained can be sealed to form a bag. The irradiation bag has a substantially flat inside. In particular, the bag is made from material that has no adsorption maximum in the range of 200 to 270 nm. Thickness and quality of the EVA material after sterilization is such, that it shows minimal adsorption of UV-light. Particularly preferred are EVA polymers of low polymerisation degree and low crosslinking. The UV-Light adsorption may also be influenced by the acetylation degree of the EVA.

The volume capacity of the irradiation bag is at least 5 times and most preferred at least 10 times of the actual storage volume of PC/suspended PC stored in the bag.

The volume capacity of the irradiation bag is defined as maximum filling volume obtained by gravity flow of water into the bag at 1 m bight difference. The actual storage volume of PC is the volume, in which the PC is stored, which includes both plasma and platelet storage solution.

For example, the volume capacity of the irradiation bag is 5000 ml and the actual storage volume of PC is 500 ml. Therefore the ratio of volume capacity of the irradiation bag to PC volume is factor 10. Consequently, the irradiation bag is not completely filled with PC. The irradiation bag is filled at most 20% and preferably 1 to 10% and most preferred 1 to below 10% (each in Vol. %) of its capacity with biological fluid.

Therefore the irradiation bag after filling with PC is only a few millimeters thick, such as less than 5 mm. For example bags of a dimension of 19×38 cm filled with 200 to 300 ml of PC have a thickness of below 5 mm. It is preferred that time tubes entering into the bag have small diameters. Also to improve agitation and homogenous mixing of PC, the inside of the irradiation bag preferably comprises cut off or rounded corners. When viewed from the top, the inside of the irradiation bag have at least 4, preferably 5 or even 8 corners or forms a circle or oval when filled with suspended PC. So the inside of the irradiation bag has a round or oval volume when filled.

According to a preferred embodiment of the invention, the irradiation bag has one ore more inlet tubes for filling the PC into the irradiation bag and optionally one ore more outlet tubes for discharging the irradiated PC into the storage bag. The irradiation bag is further provided with means for preventing fluid access into the inlet and/or outlet tubes such that no dead area is formed inside the bag.

For example, it is advisable to have the inlet side of the bag clamped off or sealed off after filling of the bag with the PC to avoid dead areas of the irradiation bag. The sealing can be performed in such a manner, that the corner is cut off and therefore lies a shape of a rounded corner or similar to a rounded corner.

In that case, the inlet tube is preferably located at one corner of the irradiation bag, between the two plastic foils forming the irradiation bag. When the inlet side of the bag is clamped off or sealed after filling, a sealed compartment is formed into which the inlet tube opens. The sealed compartment preferably does not contain PC and is separated from the main compartment of the bag containing the PC.

To facilitate the sealing of the corner of the bag, the irradiation bag comprises a partial seal extending from one edge of the bag to an adjacent edge thereto, thereby partially enclosing the opening of the inlet tube.

The outlet opening may preferably contain a clamp off part or break-off part, so that no PC can enter into the outlet tube. After irradiation the outlet part or break-off part is opened, so that the irradiated, pathogen inactivated PC can be transferred through the tube 3 into the storage bag (see FIG. 3 and FIG. 4).

At the bottom the bag may additionally have an area where a bag label or a let number may be placed. Such area is not used for storing PC and is outside the area of irradiation since it is beneficial to irradiate the irradiation bag from both sides of the bag.

The storage bag may be made from PVC material comprising DEHP, citrate esters or Triociyl trimellitate (TOTM) as plasticizer. However, according to a preferred embodiment the storage bag consists of the same UV-transparent plastic material as the irradiation bag.

It is important that the storage bag shows gas permeability, in particular oxygen and carbon dioxide permeability, and platelet compatibility, so that the PC can be stored for up to 10 days preferably under a slight agitation.

The bag system may be sterilized by standard techniques like steam or ethylene oxide treatment or by β-rays irradiation, so that the bags and tubes allow sterile preparations after pathogen reduction.

It was also found that optionally at least part of the plasma contained in the PC may be substituted by an aqueous salt solution to form a suspended PC, which is suitable for platelet storage. A preferred aqueous salt solution is SSP+ as marketed by MacoPharma. The plasma in the PC to be irradiated may be substituted by 50 to 95 weight %, preferably 70 to 80 weight % with SSP+.

However, other suitable platelet storage solutions may also be used, which replace the plasma for storage. Optimal storage of PC in storage bag is characterized by in vitro parameters like swirling, pH, osmotic stability and aggregation, as described in table 1. With the platelet storage solution UV-irradiation, mixing of the partially plasma exchanged PC agitation of the irradiation bag and storage in the storage bag is optimal.

Results of pathogen reduction efficiency are described in the above mentioned co-pending German patent application No. 10 2005 062 410.3 by the present applicant and Forschungsgemeinschaft der DRK-Blutspendedienst e.V., filed 23 Dec. 2005 and are incorporated herein by reference.

UV-irradiation is ideally performed from both sides of the bag, preferably at the same time. UV-irradiation must be at least partially accompanied by agitation of the irradiation bag. Agitation must be such that a homogenous mixing of the PC is performed and at same time, during mixing of the PC, thicknesses of the irradiation bag must be such that the UV light penetrates through the PC.

In particular, the irradiation bag is agitated while irradiated by means of a steady agitation using an amplitude of from 0.2 to 8 cm in the x and the y direction of the plane, and a frequency of the amplitude from 10 to 200 Hz. In a preferred embodiment, x and y are the same and the path is circular.

Light of wavelengths in between 200 to 400 nm covering UV-A, UV-B and UV-C is used for irradiation. It was found, however, that the UV-light suited best for the procedure is UV-C-light with frequencies between 200 to 350 nm, in particular 200 to 270 nm.

The UV-C-light used may also contain components of UV-B and UV-A as well as visible light components. According to a preferred embodiment monochromatic UV-C-light, with an emission maximum of 254 nm is used.

The light dose for irradiation may be between 0.01 and 2 $J/cm^2$, however, depending on the frequency range and filters used and the PC layer thickness in the illumination bag, other energies are possible. This also depends on whether the light has been generated by a quartz lamp, light emitting diodes (LEDs) or flash lights, e.g. by Eximer lamps.

DESCRIPTION OF THE FIGURES

The invention is illustrated by the figures without being limited to the embodiment depicted.

Figure 1:
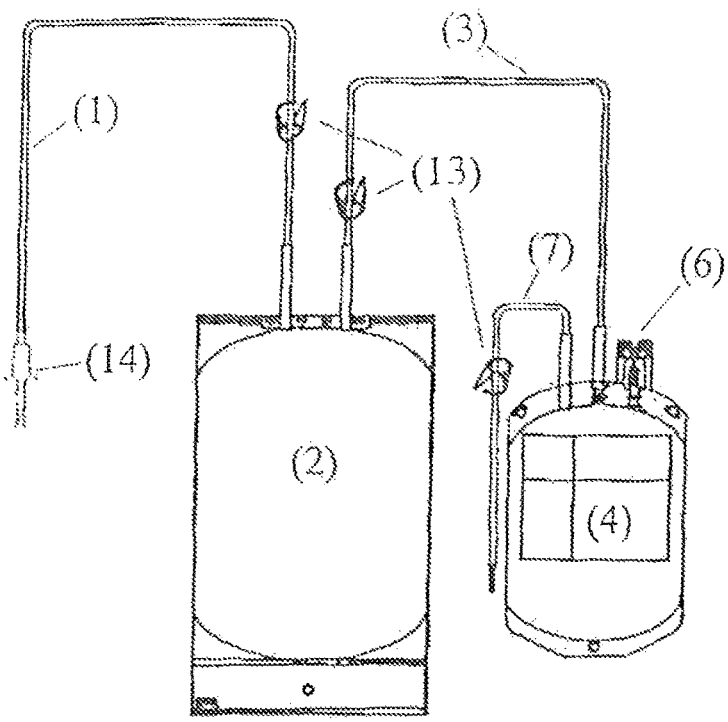
FIG. 1 shows a blood bag system according to the invention.

The plastic double bag system shown in FIG. 1 comprises an inlet tube 1 connected to the irradiation bag 2 to sample the incoming stream of the processed PC co uprising platelet storage solution. The irradiation bag 2 is connected through a second tube 3 to a storage bag 4, used for storage and administering the blood product to a patient in need for platelets. After irradiation of the PC in the irradiation bag 2 and transfer of its content to the storage bag 4 through the tube 3, the tube 3 is sealed off and thus the irradiation bag 2 is separated from the storage bag 4. The storage bag 4 comprises a port 6 for spikes and optionally an additional third tube 7, which may be used for sampling, under which circumstances the third tube 7 may be connected to a sampling bag 10.

Figure 2:
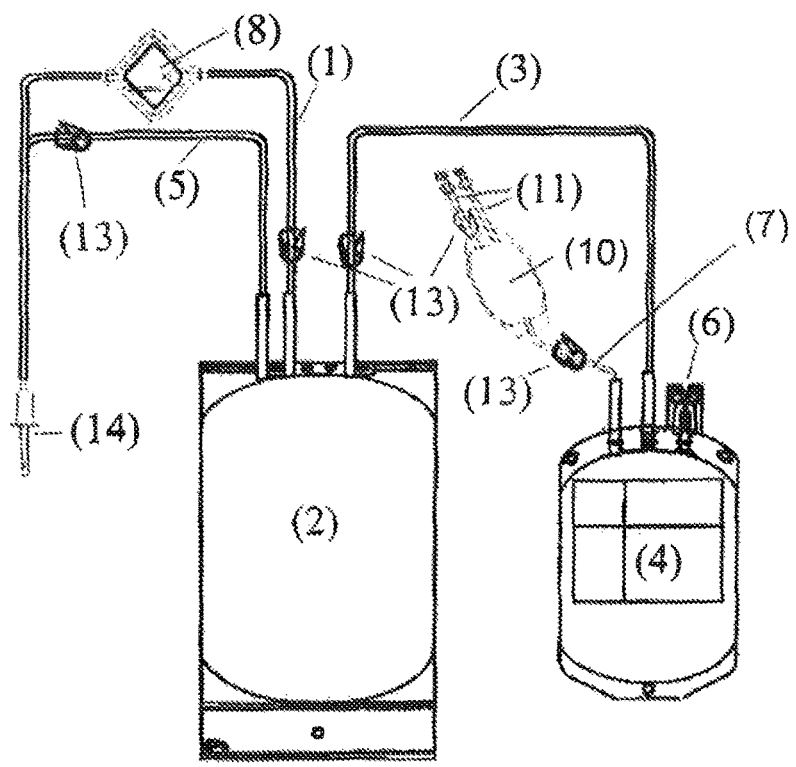
FIG. 2 shows a further embodiment of the blood bag system of FIG. 1 additionally comprising a leucocyte filter and a sampling bag.

A further embodiment of the blood bag system is schematically depicted in FIG. 2. Beside the elements described in FIG. 1, the blood bag system further comprises a leucocyte filter 8 included in the inlet tube 1. This leucocyte filter may be bypassed by a bypass tube 5 further allowing air venting of the irradiation bag 2.

The sampling bag 10 allows the early and late detection of contaminants in PC, as explained in the above mentioned FR 200506296. Briefly, at the time of the filling of the storage bag 4, a sample of PC is transferred into the sample bag 10. Before the storage of the PC, a first contamination test is performed on a first part of the sampled PC, the first part being taken from the sample bag 10 via a first outlet 11.

If no contamination is detected, the PC is stored. Before the transfusion of the PC to a patient, a second contamination test is performed on a second part of the sampled PC taken from the sample bag 10 via a second outlet 11.

The bags in the blood bag system as shown in FIGS. 1 and 2 further have clamps or break-off parts 13 to close or otherwise allow free flow of the platelet concentrate through the tubing.

Figure 3:
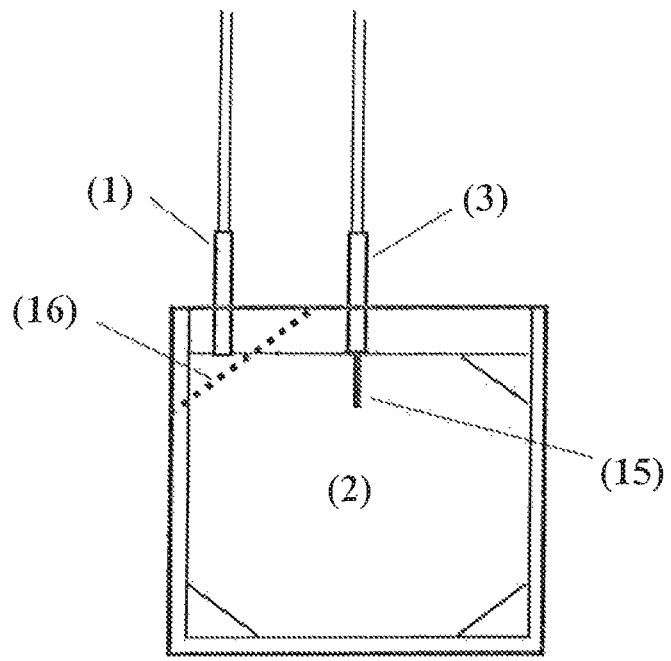
FIG. 3 shows an embodiment, where details of the bag size and of the inlet and outlet tube of the irradiation bag are depicted.

FIG. 3 depicts a variation of the irradiation bag 2 of FIG. 1. In this figure, the inlet tube 1 is moved to the one corner of the bag, which does not show any corner cut-off inside the bag. Once the PC has been filled into the bag, this part may be sealed off along the line 16, which can be placed using a suitable heat seal or high frequency sealing system to result in cut-off corner of the bag. The reason to have the corner of the irradiation bag rounded or cut-off, is not to have dead areas during the agitation and irradiation steps described above.

This preferred embodiment shows also a break-off part 15, which closes the tube 3 and which might be opened after irradiation, thus allowing free flow of the irradiated PC through the tube 3 into the storage bag. This break-off part is constructed and placed into the bag such, that no dead areas do exist, in which PC is trapped and not agitated during the irradiation process. This break-off part may be substituted by any system suitable for closing and opening of bags, like ball valves, plugs or other systems.

The embodiment shown in FIG. 3 shows a bag having a square format, where the length and the height of the bag are almost the same. The inside forms an octagon. Bag 2 can also be constructed as a circular bag, containing in- and outlets.

Octagon type and circular top views of the inside boundaries have advantages on agitation by reducing possible dead ends even further, especially on circular or elliptic horizontal agitation. Therefore the bag (2) is suitable for illumination, storage and transfusion of PC.

For routine use tube 1 is sterilely docked to a PC source, obtainable from blood donations by apheresis or by a buffy-coat pool procedure. For connection purposes the inlet tube 1 may contain spike (14).

Figure 4:
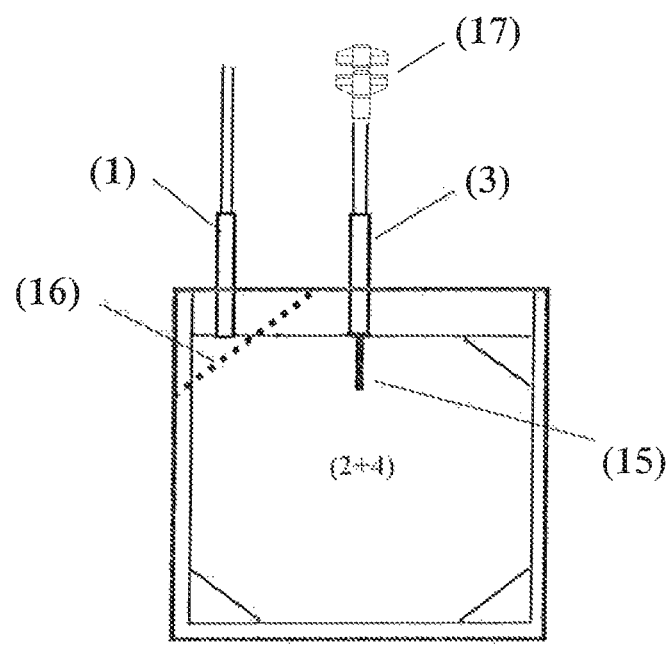
FIG. 4 shows a different embodiment, wherein the irradiation bag and the storage bag form one bag.

Bag 2+4 shown in FIG. 4 may be used as storage bag 2 and irradiation bag 4 at the same time. In addition to the features described for the embodiment of FIG. 3, additionally comprised is a closure 17 in form of a part which allows connection with spikes of transfusion sets.

Figure 5:
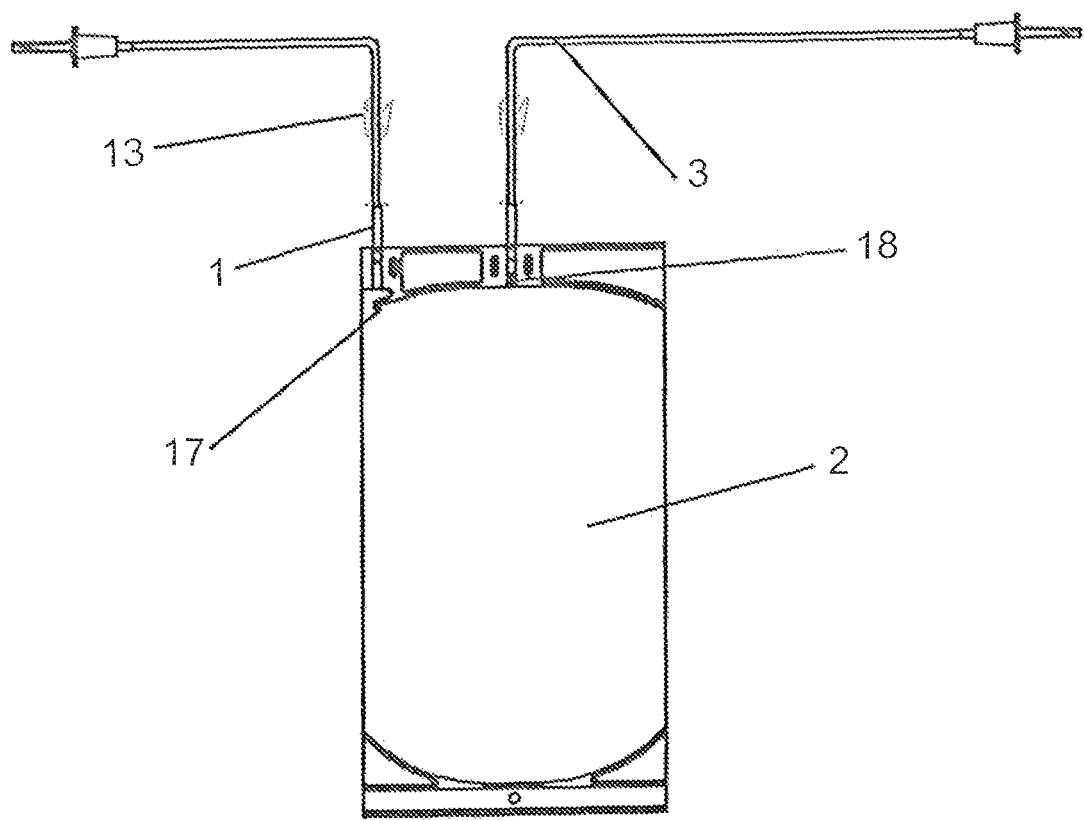
FIG. 5 shows a different embodiment of the irradiation bag of the blood bag system.

Another example of the irradiation bag is illustrated in FIG. 5. The irradiation bag 2 is provided with an inlet tube 1 for filling the bag with PC/suspended PC and an outlet tube 3 for discharging the PC/suspended PC into a storage bag.

The irradiation bag 2 comprises a partial seal 17 extending from one edge of the bag to an adjacent edge thereof. When the seal is completed, for example by using a hand held sealer, the seal creates a first sealed compartment enclosing the opening of the inlet tube 1 and a second sealed compartment comprising the PC/suspended PC. This first sealed compartment prevents the PC contained in the second sealed compartment to enter the inlet tube 1. In that way, the bag does not contain any dead area, ensuring that all PC is agitated and irradiated during the inactivation process.

Moreover, as shown in FIGS. 3 to 5, the seal 16,17 enclosing the inlet tube 1 at one edge of the irradiation bag 2 is symmetrical to at least another edge, thereby providing a symmetrical irradiation bag. This particular shape improves the agitation of the content of the bag.

Advantageously, the irradiation bag also comprises an outlet tube provided with a plug 18, ensuring that no PC/suspended PC enters the outlet tube. For discharging the PC into the storage bag, the plug 18 is simply removed from the outlet tube 3 by pressing manually the outlet tribe to expel the plug 18 into the bag.

It is apparent to the skilled reader that the blood bag system and the method described herein and in particular with reference to FIG. 1 to FIG. 5 can as well be applied to reduce pathogens in other biological fluids such as platelet lysates, stem cell suspensions, tissue culturing media, plasma, plasma and proteins solutions. For such applications the reference to PC or suspended PC in this application may be exchanged against any one of above biological fluids. Furthermore the term "blood bag system" itself is not intended to limit the bag or the method disclosed herein to a use in connection with biological fluids that ale derived from blood only. Except that the suspended PC is exchanged against the other biological fluids all features described in more detail in the general part hereinbefore are applicable as well.

For example it should be noted that the procedure and bag system as described herein and in particular with reference to any of the claims can be used for pathogen reduction of plasma alone without the presence of PC. Therefore therapeutic quantities of human plasma and plasma protein solutions (such as from 100-350 ml, and up to 700 ml) can also be pathogen reduced using UV-light and the above mentioned procedure.

Experimental Part

A preferred bag system and procedure uses a first bag with the size of an irradiation surface of 19×38 cm, consisting of a flexible EVA-sheeting with 0.25 mm thickness, with min. UV-adsorption characteristics. The irradiation bag is filled with 300 ml of suspended PC with $4\times10^{11}$ platelets, leukodepleted to less than $10^6$ residual leucocytes per PC, in plasma, where 70 weight % of the plasma has been replaced by SSP+ by MacoPharma as Storage Solution for PC. The SSP+ solution comprises (in g/l):

Na-Citrate $2H_2O$: 3.18; Na-Acetate $3H_2O$: 4.42; Na-Phosphate $2H_2O$: 1.05; Di-Na-Phosphate: 3.05; KCl: 0.37; $MgCl_2 6H_2O$: 0.3; NaCl: 4.05 and Water to 1000 ml.

The PC in bag was irradiated horizontally for a period of 2 min. from both sides at the same time, using an UVC irradiation machine with quartz tubes, VIS-light filter, under orbital agitation of the bag at 100 Hz with amplitude of 2 cm in one axis and 4 cm in the other axis at room temperature. We found that orbital mixing is preferred over circular mixing. Under these conditions a homogeneous mixing of the PC is reached. At the same time the fluid shows a profile with high and very low liquid thickness in the flexible bag with a distribution of moving and standing waves in the bag.

After the irradiation step, the treated PC was transferred into the second bag, which consisted of a 1000 to 1500 ml bag of EVA (Alternatively PVC/TOTM sheering may be used), allowing sufficient gas exchange for $CO_2$ and $O_2$ during up to 10 days storage, under slight horizontal agitation at room temperature.

In the practical example an irradiation and a storage bag made from EVA was used and the irradiation bag was irradiated with UV-C radiation at a rate of 0.6 $J/cm^2$ under constant agitation.

The results of the procedure applied to PC in the blood bag system according to the invention are summarized in Table, 1. These results demonstrate that the PC quality does not change significantly by the treatment or after storage for several days.

This inactivation method does not require the addition of an inactivating substance, such as photosensitive or photodynamic active substance, in the biological fluid to be treated. No further step, e.g. removal of the inactivating substance, is necessary. It is acknowledged that UVC directly activates nucleotides of viruses and bacteria, without the need of exogenous substances.

TABLE 1

Platelet parameters during storage with and without treatment at 100 Hz, under orbital agitation and UVC-irradiation in SSP+ platelet storage solution

| | Before treatment | Day 6* (treatment) | | Day 8* (treatment) | |
|---|---|---|---|---|---|
| | | Without | with | without | With |
| Platelets ($10^8$/ml) | 11.2 | 9.98 | 10.4 | 10.8 | 10.5 |
| pH | 7.03 | 7.14 | 7.13 | 7.19 | 7.10 |
| HSR (%) | 54 | 58 | 62 | 61 | 61 |
| Swirling (grade) | 5 | 5 | 5 | 5 | 5 |
| Aggreg. (%) | 87 | 87 | 86 | 82 | 86 |

USR: Hypotonic Shock Reaction
Swirling: Visual inspection, 0 no swirling, 5 max. swirling
Aggregation: Aggregation of platelets, collagen-induced
*storage at room teinperature

The invention claimed is:

1. A process for manufacturing a sealed irradiation bag partially filled with a platelet concentrate, the process comprising at least:
    providing a platelet concentrate from human blood donations by apheresis techniques or by buffy-coat pooling techniques;
    providing an irradiation bag made from a flexible plastic material substantially transparent to UV irradiation and comprising when viewed from inside at least three rounded corners and one or more inlet tubes and optionally one or more outlet tubes;
    introducing the platelet concentrate into the irradiation bag via the one or more inlet tubes in order to provide a partially filled irradiation bag so that the irradiation bag when sealed is filled by less than 20 vol % with the platelet concentrate;
    providing a sealing thereby providing a compartment containing the platelet concentrate to be treated and a compartment separated therefrom comprising the inner end(s) of the one or more inlet tubes,
    wherein the sealing provided comprises a rounded corner, when viewed from inside, that is symmetrical to at least one of the other rounded corners of the irradiation bag.

2. The process according to claim 1, wherein the one or more outlet tubes are provided with means for preventing the biological fluid contained in the irradiation bag and to be treated to enter into and/or to access the outlet tubes to avoid dead areas formed inside the irradiation bag in or around the outlet tubes.

3. The process according to claim 1, wherein the one or more outlet tubes comprise at least one clamp-off part, plug or break-off part as a closing for the tube end extending into the irradiation bag.

4. The process according to claim 1, wherein the irradiation bag when sealed is partially filled from less than 10 vol % to 1 vol %.

5. The process according to claim 1, wherein the separated compartment comprises one inlet tubes only.

6. The process according to claim 1, wherein the platelet concentrate contained in the irradiation bag does not contain a photosensitizer having an absorption maximum in the range of 200 to 350 nm.

7. The process according to claim 1, wherein the platelet concentrate is a suspended platelet concentrate comprising plasma wherein at least 20 weight % of the plasma contained in the platelet concentrate is exchanged against a platelet storage solution to form a suspended platelet concentrate and the platelet storage solution comprises water and soluble salts.

8. The process according to claim 7, wherein greater 50 weight % of the plasma is exchanged against a platelet storage solution.

9. The process according to claim 7, wherein the platelet storage solution contains at least one of the following salts: citrate, phosphate and/or acetate.

10. The process according to claim 1, wherein the platelet concentrate comprises 0.2 to 2.5×10$^9$ platelets per ml biological fluid contained in the irradiation bag.

11. The process according to claim 1, further comprising that the platelet concentrate is irradiated in the irradiation bag with UV-C radiation and is filled thereafter into a storage bag for storage, wherein the irradiation bag is different from the storage bag, wherein the storage bag has half or less of the volume capacity of the irradiation bag and wherein a tubing for interconnecting the irradiation bag and the storage bag, optionally detachable, is provided thereby forming a blood bag system.

12. The process according to claim 11, wherein the storage bag has 20% or less of the volume capacity of the irradiation bag.

13. The process according to claim 11, wherein the irradiation bag and the storage bag consist of the same plastic material.

14. The process according to claim 11, wherein the irradiation bag and the storage bag consist of different plastic materials.

15. The process according to claim 1, wherein at least the irradiation bag consists of EVA.

16. The process according to claim 1, wherein the storage bag is permeable for at least one gas, selected from the group consisting of air, oxygen and carbon dioxide.

17. The process according to claim 1, wherein the irradiation bag is made from material that has no adsorption maximum in the range of 2.00 to 350 nm.

18. The process according to claim 1, wherein the irradiation bag has a flat inside, the inside having boundaries when viewed from the top form a circle or oval when filled with the biological fluid.

19. The process according to claim 1, further comprising a leucocyte filter optionally as part of the inlet tube for the irradiation bag.

20. The process according to claim 1, wherein the at least one inlet tube is located at one corner of the irradiation bag.

21. The process according to claim 1, further comprising the following steps:
irradiating the irradiation bag comprising the platelet concentrate with an irradiation source comprising UV-C radiation of a wavelength of 200 to 270 nm while keeping the irradiation bag under agitation; and
inserting the irradiated platelet concentrate into a storage bag for storage or remaining the irradiated platelet concentrate in the irradiation bag for storage in the irradiation bag.

22. A process according to claim 21, comprising the following further step:
exchanging at least 20 weight % or at least 50 weight %, of the plasma contained in the platelet concentrate against a platelet storage solution to form a suspended platelet concentrate, the platelet storage solution comprises water and one or more soluble salts before exposing the platelet concentrate to UV irradiation.

23. The process according to claim 21, wherein the UV-irradiation is generated by a quartz lamp, a LED- and/or flash-light lamp.

24. The process according to claim 21, wherein the irradiation bag is placed upon a stiff sheet, optionally made from glass/quartz material, while irradiated and agitated.

25. The process according to claim 21, wherein the filled irradiation bag has an average thickness of less than 5 mm, or less than 2.5 mm, when irradiated.

26. The process according to claim 21, wherein the irradiation bag is agitated to homogeneously mix the fluid content and/or to obtain a fluid profile with wave like surface areas in the irradiation bag comprising a multiplicity of moving or standing troughs and crests, wherein the troughs at their lowest spot have average film thickness of less than 2.5 mm.

27. The process according to claim 21, wherein the light dose for irradiation of the irradiation bag is between 0.01 and 2 J/cm$^2$.

28. The process according to claim 21, wherein the platelet concentrate/suspended platelet concentrate is stored at room temperature for at least 8 days.

29. The process according to claim 21, wherein the stored platelet concentrates/suspended platelet concentrates are stored at room temperature under slight agitation for at least 8 days.

30. The process according to claim 21, wherein the irradiation bag is agitated while irradiated by means of a steady agitation using an amplitude of from 0.2 to 8 cm in the x and the y direction of the plane, wherein x and y are the same, and a frequency of the amplitude from 10 to 200 Hz.

31. The process according to claim 21, wherein the platelet concentrate contained in the irradiation bag does not contain a photosensitizer having an absorption maximum in the range of in particular 200 to 350 nm and is free of any pathogen inactivating substance added to the biological fluid or any photosensitizer.

32. The process according to claim 31, wherein the irradiation bag is irradiated and agitated while stretched out flat and horizontal on a substantially plane sheet without any clamping of the upper layer of the irradiation bag thus allowing the upper layer to freely move in reaction to the agitation of the bag.

33. The process according to claim 1, wherein the at least one inlet tube is located at one corner of the irradiation bag, the opening of the inlet tube being partially enclosed by a partial seal that can be completed to create a sealed compartment comprising the opening of the inlet tube.

* * * * *